United States Patent
Kong et al.

(10) Patent No.: US 6,395,531 B1
(45) Date of Patent: May 28, 2002

(54) METHOD FOR CLONING AND EXPRESSION OF MLYI RESTRICTION ENDONUCLEASE AND MLYI METHYLASE AND BSTNBII METHYLASE IN E. COLI

(75) Inventors: Huimin Kong, Wenham; Lauren Sears Higgins, Essex, both of MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/814,134

(22) Filed: Mar. 21, 2001

(51) Int. Cl.⁷ .............................. C12N 9/22; C12N 15/55
(52) U.S. Cl. ................. 435/199; 435/252.3; 435/320.1; 536/23.2
(58) Field of Search .............................. 435/199, 320.1, 435/252.3; 536/23.2

(56) References Cited

U.S. PATENT DOCUMENTS

| | | | |
|---|---|---|---|
| 5,200,333 A | 4/1993 | Wilson | 435/172.3 |
| 5,498,535 A | 3/1996 | Fomenkov et al. | 435/172.3 |
| 6,191,267 B1 * | 2/2001 | Kong et al. | 536/23.4 |

OTHER PUBLICATIONS

Higgins, L.S, et al. (2001) Nucl. Acids Res. 29(12), 2492–2501.*
Blumenthal, et al., J. Bacteriol. 164:501–509 (1985).
Bougueleret, et al., Nucl. Acids Res. 12:3659–3676 (1984).
Theriault and Roy, Gene 19:355–359 (1982).
Fomenkov, et al., Nucl. Acids Res. 22:2399–2403 (1994).
Gingeras and Brooks, Proc. Natl. Acad. Sci. 80:402–406 (1983).
Janulaitis, et al., Gene 20: 197–204 (1982).
Kiss, et al., Nucl. Acids Res. 13:6403–6421 (1985).
Kiss and Baldauf, Gene 21:111–119 (1983).
Kosykh, et al., Mol. Gen. Genet. 178:717–718 (1980).
Malone, et al., J. Mol. Biol. 253:618–632 (1995).
Mann, et al., Gene 3:97–112 (1978).
New England Biolabs' catalog 2000–2001, p. 220.
Roberts, et al., Nucl. Acids Res. 27:312–313 (1999).
Szomolanyi, et al., Gene 10:219–225 (1980).
Walder, et al. J. Biol. Chem. 258:1235–1241 (1983).
Walder, et al., Proc. Natl. Acad. Sci. USA 78:1503–1507 (1981).
Wayne, et al., Gene 202–83–88 (1997).

* cited by examiner

*Primary Examiner*—Charles L. Patterson, Jr.
(74) *Attorney, Agent, or Firm*—Gregory D. Williams

(57) ABSTRACT

The present invention relates to recombinant DNA which encodes the MlyI restriction endonuclease as well as the MlyI and BstNBII methyltransferases and expression of MlyI restriction endonuclease and M.BStNBII in *E. coli* cells containing the recombinant DNA.

5 Claims, 6 Drawing Sheets

R: restriction endonuclease gene, mlyIR
M: modification methylase gene, mlyIM

Figure 2-1

```
              10                  30                  50
ATGAACTCTCTATCACCATCTAGCTATACTGCTGAGTTAAATTTTGAATATAAATCAGAT
MetAsnSerLeuSerProSerSerTyrThrAlaGluLeuAsnPheGluTyrLysSerAsp 70                  90                 110
GATAACAGTCCCAGACGCATATCAATTCAGCGCAATGATGTAATTTCGTTTTTAAAAAGT
AspAsnSerProArgArgIleSerIleGlnArgAsnAspValIleSerPheLeuLysSer 130                 150                 170
CTGCCTGACAATAGTGTTGATGTATTAATAACAGATCCTGCTTATTCAGGAATGAATAAT
LeuProAspAsnSerValAspValLeuIleThrAspProAlaTyrSerGlyMetAsnAsn 190                 210                 230
AAATTAAAACTCGGTAAAGGACGGATTGTTGGAAAATATGCTGATAAAGGTACAGAACAA
LysLeuLysLeuGlyLysGlyArgIleValGlyLysTyrAlaAspLysGlyThrGluGln 250                 270                 290
GCTAAATGGTTCAATGAATTTGATGATACAGAAGAAAATTACCATCAGTTTTTAAGTGAA
AlaLysTrpPheAsnGluPheAspAspThrGluGluAsnTyrHisGlnPheLeuSerGlu 310                 330                 350
TGTAAAAGAGTCTTAAATAAGCAAACAGGTCATATTTATTTAATGTTTGACTCCTTCAGT
CysLysArgValLeuAsnLysGlnThrGlyHisIleTyrLeuMetPheAspSerPheSer 370                 390                 410
TTATTAACTTTAGGGGCATTAGTACGAGAGTATTTTGATGTAAAAAACTTGYTCGTATGG
LeuLeuThrLeuGlyAlaLeuValArgGluTyrPheAspValLysAsnLeuXxxValTrp 430                 450                 470
GACAAAGTAAACATTGGAATGGGACACTATTTCCGTCGACGCCATGAATTAATTTTGTTT
AspLysValAsnIleGlyMetGlyHisTyrPheArgArgArgHisGluLeuIleLeuPhe 490                 510                 530
GCTACAAATGGTAACACTCGAAAAGTAAGCAGTAGATCTCTGCATGATATTTGGGATGTA
AlaThrAsnGlyAsnThrArgLysValSerSerArgSerLeuHisAspIleTrpAspVal 550                 570                 590
AAGCGTATTCATAACTCGAAATACCCAACTCAAAAACCGGTAGAGGTTTTTGAACGTATG
LysArgIleHisAsnSerLysTyrProThrGlnLysProValGluValPheGluArgMet 610                 630                 650
CTTGAGGCTAGTAGTATTCCTGGTTTTACAGTTTGTGATCCATTTCTAGGTAGTGGTTCA
LeuGluAlaSerSerIleProGlyPheThrValCysAspProPheLeuGlySerGlySer 670                 690                 710
GCGGCTCTTGCGGCTATTAAATATGATTGTAACTTTGTTGGTTGCGACATTTCAGAACAA
AlaAlaLeuAlaAlaIleLysTyrAspCysAsnPheValGlyCysAspIleSerGluGln 730                 750                 770
TCTTTTGAATTATGTAGTGAAAGAATCCAACAATTTCTAGATAATAACGTGGATATCTTG
SerPheGluLeuCysSerGluArgIleGlnGlnPheLeuAspAsnAsnValAspIleLeu
```

Figure 2-2

```
     790
GAAAAGAGTTCTAAAAGTAA
GluLysSerSerLysLysEnd
```

Figure 3-1

```
                10                      30                      50
ATGGCATCGTTATCAAAGACTAAACATTTATTTGGTTTTACTTCACCACGAACAATTGAA
MetAlaSerLeuSerLysThrLysHisLeuPheGlyPheThrSerProArgThrIleGlu 70                      90                     110
AAAATTATTCCAGAATTAGATATATTGAGCCAACAATTTTCTGGAAAGGTATGGGGTGAA
LysIleIleProGluLeuAspIleLeuSerGlnGlnPheSerGlyLysValTrpGlyGlu 130                     150                     170
AACCAAATAAATTTCTTTGATGCGATATTTAACTCGGATTTCTATGAGGGGACCACGTAC
AsnGlnIleAsnPhePheAspAlaIlePheAsnSerAspPheTyrGluGlyThrThrTyr 190                     210                     230
CCTCAAGATCCCGCTTTAGCTGCCCGTGATAGGATAACTAGAGCTCCTAAAGCACTAGGA
ProGlnAspProAlaLeuAlaAlaArgAspArgIleThrArgAlaProLysAlaLeuGly 250                     270                     290
TTTATTCAATTAAAGCCAGTTATCCAATTGACTAAAGCGGGTAATCAACTAGTAAATCAA
PheIleGlnLeuLysProValIleGlnLeuThrLysAlaGlyAsnGlnLeuValAsnGln 310                     330                     350
AAGAGGTTACCAGAGTTATTTACAAAACAATTGCTTAAATTTCAGCTACCTTCACCCTAC
LysArgLeuProGluLeuPheThrLysGlnLeuLeuLysPheGlnLeuProSerProTyr 370                     390                     410
CATACACAATCACCCACAGTAAATTTTAATGTTCGTCCTTACCTTGAGTTACTTCGATTA
HisThrGlnSerProThrValAsnPheAsnValArgProTyrLeuGluLeuLeuArgLeu 430                     450                     470
ATCAATGAATTAGGTTCTATATCTAAAACGGAAATAGCTTTATTTTTTCTTCAATTAGTT
IleAsnGluLeuGlySerIleSerLysThrGluIleAlaLeuPhePheLeuGlnLeuVal 490                     510                     530
AATTACAATAAATTTGATGAGATAAAAAATAAGATTTTAAAATTTAGAGAAACGAGAAAA
AsnTyrAsnLysPheAspGluIleLysAsnLysIleLeuLysPheArgGluThrArgLys 550                     570                     590
AATAATCGCAGTGTTAGTTGGAAGACTTATGTTTCACAAGAATTTGAAAAGCAGATTTCT
AsnAsnArgSerValSerTrpLysThrTyrValSerGlnGluPheGluLysGlnIleSer 610                     630                     650
ATTATTTTTGCAGATGAAGTAACAGCAAAAAACTTTAGAACTAGAGAAAGTTCTGATGAA
IleIlePheAlaAspGluValThrAlaLysAsnPheArgThrArgGluSerSerAspGlu 670                     690                     710
TCTTTTAAAAAATTTGTAAAAACTAAAGAAGGGAATATGAAGGACTATGCAGATGCATTT
SerPheLysLysPheValLysThrLysGluGlyAsnMetLysAspTyrAlaAspAlaPhe 730                     750                     770
TTCCGTTATATTCGGGGGACACAGTTAGTTACTATTGATAAAAACCTCCATCTTAAAATA
PheArgTyrIleArgGlyThrGlnLeuValThrIleAspLysAsnLeuHisLeuLysIle
```

Figure 3-2

```
             790                  810                  830
TCTAGTTTAAAACAGGACAGTGTTGATTTTTTATTAAAAAATACGGATCGTAATGCTTTA
SerSerLeuLysGlnAspSerValAspPheLeuLeuLysAsnThrAspArgAsnAlaLeu 850                  870                  890
AATCTAAGTTTAATGGAATATGAAAATTATCTTTTTGATCCANATCAGTTAATCGTTCTT
AsnLeuSerLeuMetGluTyrGluAsnTyrLeuPheAspProXxxGlnLeuIleValLeu 910                  930                  950
GAANATAATAGTGGACTTATTAATAGTAAAATTAAGCAGTTAGACGATTCTATAAATGTA
GluXxxAsnSerGlyLeuIleAsnSerLysIleLysGlnLeuAspAspSerIleAsnVal 970                  990                 1010
GAATCTTTGAAAATTGATGATGCGAAAGATTTATTAAATGATCTGGAAATCCAGCGAAAA
GluSerLeuLysIleAspAspAlaLysAspLeuLeuAsnAspLeuGluIleGlnArgLys 1030                 1050                 1070
GCTAAAACTATAGAAGATACTGTTAACCATTTAAAACTTAGATCTGATATTGAAGATATT
AlaLysThrIleGluAspThrValAsnHisLeuLysLeuArgSerAspIleGluAspIle 1090                 1110                 1130
TTAGACGTCTTTGCAAAAATTAAGAAAAGAGATGTCCCAGATGTTCCTTTATTCCTTGAA
LeuAspValPheAlaLysIleLysLysArgAspValProAspValProLeuPheLeuGlu 1150                 1170                 1190
TGGAATATATGGAGAGCTTTTGCTGCACTAAATCATACACAAGCGATAGAAGGGAACTTC
TrpAsnIleTrpArgAlaPheAlaAlaLeuAsnHisThrGlnAlaIleGluGlyAsnPhe 1210                 1230                 1250
ATTGTAGATTTAGATGGAATGCCTTTAAATACAGCTCCAGGTAAGAAGCCTGATATAGAA
IleValAspLeuAspGlyMetProLeuAsnThrAlaProGlyLysLysProAspIleGlu 1270                 1290                 1310
ATTAATTACGGATCTTTTTCATGCATTGTTGAAGTAACTATGTCATCAGGGGAAACTCAA
IleAsnTyrGlySerPheSerCysIleValGluValThrMetSerSerGlyGluThrGln 1330                 1350                 1370
TTTAATATGGAGGGGTCTTCTGTTCCACGACATTATGGTGATTTAGTGAGAAAGGTTGAC
PheAsnMetGluGlySerSerValProArgHisTyrGlyAspLeuValArgLysValAsp 1390                 1410                 1430
CATGATGCATATTGTATATTTATAGCCCCTAAAGTTGCGCCAGGAACAAAAGCACATTTC
HisAspAlaTyrCysIlePheIleAlaProLysValAlaProGlyThrLysAlaHisPhe 1450                 1470                 1490
TTTAACTTAAATCGACTTTCAACAAAACATTATGGTGGAAAAACAAAGATTATTCCTATG
PheAsnLeuAsnArgLeuSerThrLysHisTyrGlyGlyLysThrLysIleIleProMet 1510                 1530                 1550
TCATTAGATGATTTCATATGTTTCTTACAAGTTGGGATCACACATAATTTTCAAGATATT
SerLeuAspAspPheIleCysPheLeuGlnValGlyIleThrHisAsnPheGlnAspIle
```

Figure 3-3

```
        1570                  1590                  1610
AATAAACTAAAAAATTGGTTGGACAACTTAATTAATTTCAATTTAGAAAGCGAAGATGAA
AsnLysLeuLysAsnTrpLeuAspAsnLeuIleAsnPheAsnLeuGluSerGluAspGlu 1630                  1650                  1670
GAAATTTGGTTTGAAGAAATTATAAGTAAAATTTCTACATGGGCTATATAG
GluIleTrpPheGluGluIleIleSerLysIleSerThrTrpAlaIleEnd
```

METHOD FOR CLONING AND EXPRESSION OF MLYI RESTRICTION ENDONUCLEASE AND MLYI METHYLASE AND BSTNBII METHYLASE IN E. COLI

BACKGROUND OF THE INVENTION

The present invention relates to recombinant DNA which encodes the MlyI restriction endonuclease (endonuclease) as well as the MlyI methyltransferase and the BstNBII methyltransferase (methylase). The present invention also relates to the expression of MlyI restriction endonuclease and BstNBII methylase in *E. coli* cells containing the recombinant DNA.

MlyI endonuclease and MlyI methyltransferase are found in the strain of *Micrococcus lylae* (New England Biolabs' strain collection #1170). The endonuclease (R.MlyI) recognizes the double-stranded DNA sequence 5'GAGTC 3' and cleaves DNA five bases downstream generating blunt ends. The MlyI methyltransferase (M.MlyI) recognizes the double-stranded DNA sequence 5' GASTC 3' and modifies the N6-adenine by addition of a methyl group to become N6-methyladenine in the DNA sequence.

BstNBII methylase (M.BstNBII) is found in the strain of *Bacillus stearothermophilus* 33M (New England Biolabs' strain collection #928). It also recognizes the double-stranded DNA sequence 5'GASTC 3' and modifies the N6-adenine by addition of a methyl group to become N6-methyladenine in the DNA sequence. MlyI/BstNBII sites that are N6mA modified by M.BstNBII are resistant to both BstNBII and MlyI restriction digestion.

Type II and type IIs restriction endonucleases are classes of enzymes that occur naturally in bacteria and in some viruses. When they are purified away from other bacterial/viral proteins, restriction endonucleases can be used in the laboratory to cleave DNA molecules into small fragments for molecular cloning and gene characterization.

Restriction endonucleases recognize and bind particular sequences of nucleotides (the 'recognition sequence') along DNA molecules. Once bound, they cleave the molecule within (e.g. BamHI), to one side of (e.g. SapI), or to both sides (e.g. TspRI) of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, Nucl. Acids Res. 27:312–313, (1999)).

Restriction endonucleases typically are named according to the bacteria from which they are discovered. Thus, the species *Deinococcus radiophilus* for example, produces three different restriction endonucleases, named DraI, DraII and DraIII. These enzymes recognize and cleave the sequences 5'TTT/AAA3', 5'PuG/GNCCPy3' and 5'CACNNN/GTG3' respectively. *Escherichia coli* RY13, on the other hand, produces only one enzyme, EcoRI, which recognizes the sequence 5'G/AATTC3'.

A second component of bacterial/viral restriction-modification (R-M) systems are the methylase. These enzymes co-exist with restriction endonucleases and they provide the means by which bacteria are able to protect their own DNA and distinguish it from foreign DNA. Modification methylases recognize and bind to the same recognition sequence as the corresponding restriction endonuclease, but instead of cleaving the DNA, they chemically modify one particular nucleotide within the sequence by the addition of a methyl group (C5 methyl cytosine, N4 methyl cytosine, or N6 methyl adenine). Following methylation, the recognition sequence is no longer cleaved by the cognate restriction endonuclease. The DNA of a bacterial cell is always fully modified by the activity of its modification methylase. It is therefore completely insensitive to the presence of the endogenous restriction endonuclease. Only unmodified, and therefore identifiably foreign DNA, is sensitive to restriction endonuclease recognition and cleavage. During and after DNA replication, usually the hemi-methylated DNA (DNA methylated on one strand) is also resistant to the cognate restriction digestion.

With the advancement of recombinant DNA technology, it is now possible to clone genes and overproduce the enzymes in large quantities. The key to isolating clones of restriction endonuclease genes is to develop an efficient method to identify such clones within genomic DNA libraries, i.e. populations of clones derived by 'shotgun' procedures, when they occur at frequencies as low as $10^{-3}$ to $10^{-4}$. Preferably, the method should be selective, such that the unwanted clones with non-methylase inserts are destroyed while the desirable rare clones survive.

A large number of type II and a few type IIs restriction-modification systems have been cloned. The first cloning method used bacteriophage infection as a means of identifying or selecting restriction endonuclease clones (EcoRII: Kosykh et al., Mol. Gen. Genet. 178:717–719 (1980); HhaII: Mann et al., Gene 3: 97–112 (1978); PstI: Walder et al., Proc. Nat. Acad. Sci. 78: 1503–1507 (1981)). Since the expression of restriction-modification systems in bacteria enable them to resist infection by bacteriophage, cells that carry cloned restriction-modification genes can, in principle, be selectively isolated as survivors from genomic DNA libraries that have been exposed to phage. However, this method has been found to have only a limited success rate. Specifically, it has been found that cloned restriction-modification genes do not always confer sufficient phage resistance to achieve selective survival.

Another cloning approach involves transferring systems initially characterized as plasmid-borne into *E. coli* cloning vectors (EcoRV: Bougueleret et al., Nucl. Acids. Res. 12:3659–3676 (1984); PaeR7: Gingeras and Brooks, Proc. Natl. Acad. Sci. USA 80:402–406 (1983); Theriault and Roy, Gene 19:355–359 (1982); PvuII: Blumenthal et al., J. Bacteriol. 164:501–509 (1985); Tsp45I: Wayne et al. Gene 202:83–88 (1997)).

A third approach is to select for active expression of methylase genes (methylase selection) (U.S. Pat. No. 5,200,333 and BsuRI: Kiss et al., Nucl. Acids. Res. 13:6403–6421 (1985)). Since restriction-modification genes are often closely linked together, both genes can often be cloned simultaneously. This selection does not always yield a complete restriction system however, but instead yields only the methylase gene (BspRI: Szomolanyi et al., Gene 10:219–225 (1980); BcnI: Janulaitis et al., Gene 20:197–204 (1982); BsuRI: Kiss and Baldauf, Gene 21:111–119 (1983); and MspI: Walder et al., J. Biol. Chem. 258:1235–1241 (1983)).

A more recent method, the "endo-blue method", has been described for direct cloning of thermostable restriction endonuclease genes into *E. coli* based on the indicator strain of *E. coli* containing the dinD: :lacZ fusion (Fomenkov et al., U.S. Pat. No. 5,498,535; Fomenkov et al., Nucl. Acids Res. 22:2399–2403, (1994)). This method utilizes the *E. coli* SOS response signals following DNA damage caused by restriction endonucleases or non-specific nucleases. A number of thermostable nuclease genes (TaqI, Tth111I, BsoBI, Tf nuclease) have been cloned by this method (U.S. Pat. No. 5,498,535, 1996). The disadvantage of this method is that sometimes positive blue clones containing a restriction endonuclease gene are difficult to culture due to the lack of the cognate methylase gene.

There are three major groups of DNA methyltransferases based on the position and the base that is modified (C5 cytosine methylases, N4 cytosine methylases, and N6 adenine methylases). N4 cytosine and N6 adenine methylases are amino-methyltransferases (Malone et al. J. Mol. Biol. 253:618–632 (1995)).

When a restriction site on DNA is modified (methylated) by a methylase, it is resistant to digestion by the cognate restriction endonuclease. Sometimes methylation by a non-cognate methylase can also confer the DNA site resistant to restriction digestion. For example, Dcm methylase modification of 5'CCWGG3' (W=A or T) can also make the DNA resistant to PspGI restriction digestion. Another example is that CpM methylase can modify the CG dinucloetide and make the NotI site (5'GCGGCCGC3') refractory to NotI digestion (New England Biolabs' catalog, 2000–01, page 220). Therefore methylases can be used as a tool to modify certain DNA sequences and make them uncleavable by restriction enzymes.

Because purified restriction endonucleases and modification methylases are useful tools for creating recombinant molecules in the laboratory, there is a strong commercial interest in obtaining bacterial strains through recombinant DNA techniques that produce large quantities of restriction enzymes. Such over-expression strains should also simplify the task of enzyme purification.

SUMMARY OF THE INVENTION

The present invention relates to a method for cloning the MlyI restriction endonuclease from *Micrococcus lylae* into *E. coli* by methylase selection and inverse PCR amplification of the adjacent DNA. A methylase gene with high homology to amino-methyltransferases (N6-adenine methylases) was found in the *Micrococcus lylae* DNA library after methylase selection. This gene was named MlyI methylase gene (MlyIM).

In order to clone the MlyI methylase and MlyI endonuclease genes together, partial ApoI genomic DNA fragment libraries were constructed using the pRRS vector. Methylase positive clones were obtained. However, no endonuclease activity was detected in any of the M.MlyI positive clones.

Since methylase selection failed to yield a MlyI endonuclease clone, inverse PCR was employed to amplify the adjacent downstream DNA sequence. An open reading frame was found adjacent to the mlyIM gene. This ORF was named mlyIR and was expressed in the pHKT7 vector in *E. Coli* competent ER2566 cells that contained the pIeIM-pHKUV5 plasmid. The amount of MlyI produced by this clone was virtually undetectable.

Methylase selection on the *Bacillus stearothermophilus* 33M genomic DNA had yielded a N6-adenine methylase that conferred protection against MlyI digestion when expressed in the pSYX20 plasmid. This construct was used in conjunction with a mlyIR-pUC19 plasmid in *E.coli* strain ER2502 and overexpression of mlyIR was achieved. Approximately 50,000 units were produced per gram cells.

BRIEF DESCRIPTION OF THE DRAWINGS

FIG. 2. DNA sequence of MlyI methylase gene (mlyIM, 801 bp) (SEQ ID NO:1) and its encoded amino acid sequence (SEQ ID NO:2).

FIG. 3. DNA sequence of MlyI endonuclease gene (mlyIR, 1671 bp)(SEQ ID NO:3) and its encoded amino acid sequence (SEQ ID NO:4).

DETAILED DESCRIPTION OF THE INVENTION

Figure 1:
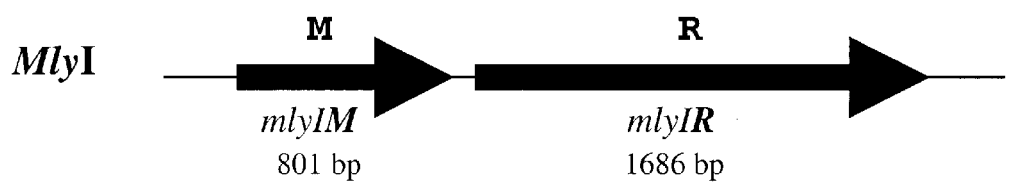
FIG. 1. Gene organization of MlyI restriction-modification system. mlyIR, MlyI restriction endonuclease gene; mlyIM, MlyI methylase gene.

The method described herein by which the MlyI methylase gene, the MlyI restriction endonuclease gene and the BstNBII methylase gene are preferably cloned and expressed in *E. coli* using the following steps:

1. Construction of *Micrococcus lylae* and *Bacillus stearothermophilus* 33M Genomic DNA Libraries and Methylase Selection Genomic DNA was prepared from *Micrococcus lylae* and *Bacillus stearothermophilus* 33M and partially digested with restriction enzymes such as ApoI and Sau3AI. The digested genomic DNA was ligated to *E. coli* cloning/expression vectors such as LITMUS 28 or pRRS with compatible ends. The ligated DNA was transformed into restriction minus *E. coli* competent cells such as RR1 and transformants were pooled and amplified. Plasmid DNA libraries were prepared and challenged with MlyI or any isoschizomer. Following digestion, the plasmids were transformed back into RR1 cells. Survivors were screened for resistance to MlyI digestion. The resistant clones were identified as methylase positive clones or plasmids that had simply lost the restriction sites. Sequencing the insert (skip to step 3) verified the cloning of a methylase gene.

2. MlyI Endonuclease Activity Assays

MlyI endonuclease activity assays were carried out using cells extracts of the M$^+$ clones. No endonuclease activity was seen.

3. Sequencing of mlyIM and bstNBIIM Genes

The mlyIM and the bstNBIIM genes were sequenced by primer walking. The mlyIM gene is 801 bp, encoding a 266-aa protein with predicted molecular mass of 30 kDa. The bstNBIIM gene is 804 bp, encoding a 267-aa protein with a predicted molecular mass of 31.1 kDa.

4. Chromosome Walking Via Inverse PCR to Isolate the MlyI Endonuclease Gene

The *Micrococcus lylae* genomic DNA was digested with 4 bp and 6 bp cutting restriction enzymes such as HpaII, Sau3AI, Taqα I and XbaI. The digested DNA was ligated at a low DNA concentration and then used for inverse PCR amplification of the mlyIR gene. Inverse PCR products were sequenced. An ORF of 1671 bp was found downstream of the mlyIM gene. This ORF is named mlyIR gene. It encodes a 556-aa protein with predicted molecular mass of 64 kDa.

5. Cloning of BstNBIIM Gene into pSYX20 to Construct a Premodified Host

The bstNBIIM gene was amplified from the genomic DNA by PCR using two primers. The PCR DNA was digested with BamHI and SalI and ligated to pSYX20. The premodified host ER2502 [pSYX20-bstNBIIM] was used for expression of the mlyIR gene in *E. coli*.

6. Expression of mlyIR Gene in Expression Vector pUC19

The HindIII and XbaI sites were incorporated into the forward primer and reverse primers for cloning of the mlyIR gene into the pUC19 expression vector. The mlyIR gene was amplified by PCR using a combination of Taq and Deep Vent DNA polymerases and primers. The PCR product was digested with HindIII and XbaI. and ligated to the pUC19 expression vector. The ligated DNA was transformed into premodified host ER2502 [pSYX20-bstNBIIM]. Plasmids with the correct size insert were screened from the transformants. Cell extracts were prepared and assayed for MlyI activity. Five out of six clones displayed high MlyI activity (>50,000 U/g cells).

The present invention is further illustrated by the following Examples. The Examples are provided to aid in the understanding of the invention and are not construed as a limitation thereof.

The references cited above and below are herein incorporated by reference.

EXAMPLE 1

Cloning of MlyI Restriction-modification System and BstNBII Modification System in *E. coli*

1. Preparation of Genomic DNA and Restriction Digestion of Genomic DNA.

Genomic DNA was prepared from *Micrococcus lylae* and *Bacillus stearothermophilus* 33M (New England Biolabs collection #1170 and 928 respectively) by the standard procedure consisting of the following steps:

(a) cell lysis by addition of lysozyme (2 mg/ml final), sucrose (1% final), and 50 mM Tris—HCl, pH 8.0

(b) cell lysis by addition of 10% SDS (final concentration 0.1%)

(c) cell lysis by addition of 1% Triton X-100 and 62 mM EDTA, 50 mM Tris—HCl, pH 8.0

(d) phenol—CHCl$_3$ extraction of DNA 3 times (equal volume) and CHCl$_3$ extraction once (e) DNA dialysis in 4 liters of TE buffer, change 3 times (f) RNA was removed by RNase A treatment and the genomic DNA was precipitated in 95% ethanol, spooled, washed, and resupended in TE buffer.

Restriction enzymes ApoI and Sau3AI were diluted by 2-fold serial dilutions. Five to ten μg genomic DNA was digested partially with ApoI and Sau3AI at 37° C. for one hour. The ApoI and Sau3AI partially digested genomic DNAs were respectively ligated to EcoRI or BamHI digested and CIP treated pRRS in the case of MlyI and LITMUS 28 in the case of BstNBII. The ligated DNA was used to transform *E. coli* RR1 competent cells by the standard procedure.

2. Construction of ApoI and Sau3AI Partial Genomic DNA Libraries and Selection of M.MlyI and M.BstNBII by the Methylase Selection Method For the transformation experiments the antibiotic ampicillin was used for selection. These transformants were pooled and spun down. Plasmid DNA was prepared from the cells using the Qiagen Qiaprep spin plasmid kit. The plasmid libraries were challenged with MlyI for 30 minutes at 37° C. followed by a 20 minute heat kill at 65° C. Following MlyI digestion, the challenged DNAs were transformed back into RR1 competent cells. Ap$^R$ survivors were screened for resistance to MlyI digestion. In the case of the *Micrococcus lylae* library, resistant clones (M.MlyI positive) were derived from both BamHI and EcoRI partial libraries. In the case of the *Bacillus stearothermophilus* 33M library, one resistant clone (M.BstNBII positive) was derived from the BamHI partial library.

3. Sequencing of mlyIM and bstNBIIM Genes

The mlyIM gene was sequenced using primer walking. The mlyIM gene is 801 bp, encoding a 266-aa protein with predicted molecular mass of 30 kDa. Sequence comparison with other methylases in GenBank indicated that M.MlyI is probably an N6-adenine methylase.

The bstNBIIM gene was sequenced using primer walking. The bstNBIIM gene is 804 bp, encoding a 267-aa protein with predicted molecular mass of 31.1 kDa. Sequence comparison with other methylases in GenBank indicated that M.BstNBII is probably an N6-adenine methylase.

4. Cloning of bstNBIIM Gene into pSYX20 to Construct a Premodified Host

Two primers were synthesized with the following sequence:

5'ATTGGATCCTAAGGAGGTGATCTAATG-GACACAGAAACTGCATCTG3' (222-47) (SEQ ID NO:5)

5'TAAGTCGACTTATTCCCAAAATACCGGTTCG3' (222-42) (SEQ ID NO:6)

The bstNBIIM gene was amplified from the genomic DNA in PCR using primers 222-47 and 222-42 under PCR conditions of 95° C. 30 sec, 50° C. 1 min, 72° C. 1 min for 20 cycles. The PCR DNA was purified through a Qiagen spin column and digested with BamHI and SalI and ligated to pSYX20 with compatible ends. One clone was found to be resistant to MlyI digestion. The premodified host ER2502 [pSYX20-BstNBIIM] was used for expression of the mlyIR gene in *E. coli*.

5. Cloning of mlyIR Gene by Inverse PCR

A) Prepare genomic DNA—For the first round of inverse PCR, 1.5 μg of bacterial DNA was digested with 100 units of TaqαI restriction endonuclease in 1×NEB TaqαI Buffer supplemented with 100 μg/ml BSA in a 50 μl reaction volume. The reaction was incubated at 37° C. for one hour, heat killed and looked at by running 13 μl on a 1% agarose gel. The digests were then circularized by incubating the remaining 37 μl (~1 μg) in 1×T4 DNA Ligase Buffer with 3000 units of T4 DNA Ligase in a 500 μl reaction volume at 16° C. overnight. A portion of this circular ligation reaction was then used as the template for subsequent inverse PCR reactions.

B) TaqαI inverse PCR reaction—A set of inverse PCR primers were synthesized based on the DNA sequence of the mlyIM gene

5'AAATTATTCCAGAATTAGATATATTG3' (222-70) (SEQ ID NO:7)

5'TCAATTGTTCGTGGTGAAGTAAA3' (222-71) (SEQ ID NO:8)

Inverse PCR was carried out using primers 222-70 and 222-71 and the above mentioned DNA templates. A 658-bp product was observed. The product was gel purified and resuspended in 30 μl dH2O. The PCR product was then sequenced using an ABI 373 automated sequencing system according to the manufacturer's instructions, using the PCR primers above as the sequencing primers. The TaqαI inverse PCR product contained approximately 280 bp of new DNA sequence.

C) HpaII, Sau3AI and XbaI inverse PCR reactions. Two inverse PCR primers complementary to newly read sequence from the TaqαI PCR product were then synthesized, as below, and used in inverse PCR reactions. Template preparation, inverse PCR, purification and DNA sequencing were performed as above but HpaII, Sau3AI and XbaI were used to create the templates as opposed to TaqαI. The sequences revealed the complete open reading frame of the mlyIR gene

5'CCACAGTAAATTTTAATGTTCGTCCT3' (224-06) (SEQ ID NO:9)

5'GTGATTGTGTATGGTAGGGTGAAGGT3' (224-05) (SEQ ID NO:10)

6. Expression of mlyIR Gene in Expression Vector pUC19

Two restriction sites (HindIII site and XbaI site) were incorporated into the forward and reverse primers, respectively for cloning of mlyIR gene into the pUC19 expression vector. Two primers were synthesized to amplify the mlyIR gene by PCR. The primers had the following sequence:

5'TTAAGCTTAAGGAGGTGATCTAATG-GCATCGTTATCAAAGACT3' (228-22) (SEQ ID NO:11)

5'ATTTCTAGACTATATAGCCCATGTAGAAATTT3' (228-23) (SEQ ID NO:12)

The mlyIR gene was amplified by PCR using a combination of Taq and Deep Vent® DNA polymerase and primers 228-23 and 228-22 under conditions of 95° C. for 30 sec, 50° C. for 1 min and 72° C. for 1.5 min. Twenty five cycles were done. The PCR product was purified by Qiagen spin column and both the PCR product and vector pUC19 were digested with HindIII and XbaI. The digested vector and PCR product were run on a 1% low melting point NuSieve agarose gel in TAE buffer. The DNA bands were cut out of the gel, and treated with β-Agarase and ethanol precipitated. The PCR DNA was then ligated to the prepared pUC19. The ligated DNA was transformed into premodified host ER2502 [pSYX20-bstNBIIM] and $AP^R$ $Kan^R$ transformants were selected for. Of 9 plasmid mini-preparations, 8 expressed MlyI activity. One of these clones with plasmid constructs pUC19-mlyIR and pSYX20-bstNBIIM was selected for producing the MlyI endonuclease. The *E.coli* strain which contains both pUC-mlyIR and pSYX20-bstNBIIM was designated as NEB #1253. The yield of recombinant MlyI in strain NEB #1253 was approximately 50,000 units/gram of cells.

pUC19 containing the MlyI restriction endonuclease gene from *Micrococcus lylae* in *Escherichia coli* ER2502 has been deposited under the terms and conditions of the Budapest Treaty with the American Type Culture Collection on Mar. 15, 2001 and received ATCC Accession No. PTA-3183.

What is claimed is:

1. Isolated DNA coding for the MlyI restriction endonuclease wherein the isolated DNA is obtainable from *Micrococcus lylae*.

2. A recombinant DNA vector comprising a vector into which a DNA segment coding for the MlyI restriction endonuclease as been inserted.

3. A host cell transformed by the vector of claim 2.

4. The host cell of claim 3 comprising ATCC Accession No. PTA-3183.

5. A method of producing a MlyI restriction endonuclease comprising culturing a host cell transformed with the vector of claim 2 under conditions suitable for expression of said endonuclease.

* * * * *

UNITED STATES PATENT AND TRADEMARK OFFICE
CERTIFICATE OF CORRECTION

PATENT NO.   : 6,395,531 B1
DATED        : May 28, 2002
INVENTOR(S)  : Xong et al.

It is certified that error appears in the above-identified patent and that said Letters Patent is hereby corrected as shown below:

Title page,
Item [57], ABSTRACT,
Line 4, replace "M.BStNBII" with -- M.BstNBII --

Coluumn 3,
Line 41, replace "(MlyIM)" with -- (mlyIM) --
Lines 51-52, replace "*E. Coli*" with -- *E. coli* --

Column 4,
Line 43, replace "Mlyl" with -- MlyI --
Line 58, replace "mlylR" with -- mlyIR --
Line 63, replace "Vent" with -- Vent® --
Line 65, replace "XbaI. and" with -- XbaI and --

Column 6,
Line 45, replace "dH20" with -- dH$_2$0 --

Column 8,
Line 4, replace "AP$^R$" with -- Ap$^R$ --

Signed and Sealed this

Eighth Day of October, 2002

*Attest:*

JAMES E. ROGAN
*Attesting Officer*          *Director of the United States Patent and Trademark Office*

SEQUENCE LISTING

<160> NUMBER OF SEQ ID NOS: 12

<210> SEQ ID NO 1
<211> LENGTH: 801
<212> TYPE: DNA
<213> ORGANISM: Micrococcus lylae
<220> FEATURE:
<221> NAME/KEY: CDS
<222> LOCATION: (1)..(798)
<223> OTHER INFORMATION: At position 412, Y = C or T

<400> SEQUENCE: 1

| atg | aac | tct | cta | tca | cca | tct | agc | tat | act | g ct | gag | tta | aat | ttt | gaa | 48 |
|---|---|---|---|---|---|---|---|---|---|---|---|---|---|---|---|---|
| Met | Asn | Ser | Leu | Ser | Pro | Ser | Ser | Tyr | Thr | A la | Glu | Leu | Asn | Phe | Glu | |
| 1 | | | | 5 | | | | | 10 | | | | | 15 | | |

| tat | aaa | tca | gat | gat | aac | agt | ccc | aga | cgc | a ta | tca | att | cag | cgc | aat | 96 |
|---|---|---|---|---|---|---|---|---|---|---|---|---|---|---|---|---|
| Tyr | Lys | Ser | Asp | Asp | Asn | Ser | Pro | Arg | Arg | I le | Ser | Ile | Gln | Arg | Asn | |
| | | | | 20 | | | | | 25 | | | | | 30 | | |

| gat | gta | att | tcg | ttt | tta | aaa | agt | ctg | cct | g ac | aat | agt | gtt | gat | gta | 144 |
|---|---|---|---|---|---|---|---|---|---|---|---|---|---|---|---|---|
| Asp | Val | Ile | Ser | Phe | Leu | Lys | Ser | Leu | Pro | A sp | Asn | Ser | Val | Asp | Val | |
| | | 35 | | | | | 40 | | | | | 45 | | | | |

| tta | ata | aca | gat | cct | gct | tat | tca | gga | atg | a at | aat | aaa | tta | aaa | ctc | 192 |
|---|---|---|---|---|---|---|---|---|---|---|---|---|---|---|---|---|
| Leu | Ile | Thr | Asp | Pro | Ala | Tyr | Ser | Gly | Met | A sn | Asn | Lys | Leu | Lys | Leu | |
| | 50 | | | | | 55 | | | | | 60 | | | | | |

| ggt | aaa | gga | cgg | att | gtt | gga | aaa | tat | gct | g at | aaa | ggt | aca | gaa | caa | 240 |
|---|---|---|---|---|---|---|---|---|---|---|---|---|---|---|---|---|
| Gly | Lys | Gly | Arg | Ile | Val | Gly | Lys | Tyr | Ala | A sp | Lys | Gly | Thr | Glu | Gln | |
| 65 | | | | | 70 | | | | | 75 | | | | | 80 | |

| gct | aaa | tgg | ttc | aat | gaa | ttt | gat | gat | aca | g aa | gaa | aat | tac | cat | cag | 288 |
|---|---|---|---|---|---|---|---|---|---|---|---|---|---|---|---|---|
| Ala | Lys | Trp | Phe | Asn | Glu | Phe | Asp | Asp | Thr | G lu | Glu | Asn | Tyr | His | Gln | |
| | | | | 85 | | | | | 90 | | | | | 95 | | |

| ttt | tta | agt | gaa | tgt | aaa | aga | gtc | tta | aat | a ag | caa | aca | ggt | cat | att | 336 |
|---|---|---|---|---|---|---|---|---|---|---|---|---|---|---|---|---|
| Phe | Leu | Ser | Glu | Cys | Lys | Arg | Val | Leu | Asn | L ys | Gln | Thr | Gly | His | Ile | |
| | | | 100 | | | | | 105 | | | | | 110 | | | |

| tat | tta | atg | ttt | gac | tcc | ttc | agt | tta | tta | a ct | tta | ggg | gca | tta | gta | 384 |
|---|---|---|---|---|---|---|---|---|---|---|---|---|---|---|---|---|
| Tyr | Leu | Met | Phe | Asp | Ser | Phe | Ser | Leu | Leu | T hr | Leu | Gly | Ala | Leu | Val | |
| | | 115 | | | | | 120 | | | | | 125 | | | | |

| cga | gag | tat | ttt | gat | gta | aaa | aac | ttg | ytc | g ta | tgg | gac | aaa | gta | aac | 432 |
|---|---|---|---|---|---|---|---|---|---|---|---|---|---|---|---|---|
| Arg | Glu | Tyr | Phe | Asp | Val | Lys | Asn | Leu | Xaa | V al | Trp | Asp | Lys | Val | Asn | |
| | 130 | | | | | 135 | | | | | 140 | | | | | |

| att | gga | atg | gga | cac | tat | ttc | cgt | cga | cgc | c at | gaa | tta | att | ttg | ttt | 480 |
|---|---|---|---|---|---|---|---|---|---|---|---|---|---|---|---|---|
| Ile | Gly | Met | Gly | His | Tyr | Phe | Arg | Arg | Arg | H is | Glu | Leu | Ile | Leu | Phe | |
| 145 | | | | | 150 | | | | | 155 | | | | | 160 | |

| gct | aca | aat | ggt | aac | act | cga | aaa | gta | agc | a gt | aga | tct | ctg | cat | gat | 528 |
|---|---|---|---|---|---|---|---|---|---|---|---|---|---|---|---|---|
| | | | | | | | | | | | | | | | | |

-continued

```
Ala Thr Asn Gly Asn Thr Arg Lys Val Ser S er Arg Ser Leu His Asp
                165                 170                 175 att tgg gat gta aag cgt att cat aac tcg a aa tac cca act caa aaa      576
Ile Trp Asp Val Lys Arg Ile His Asn Ser L ys Tyr Pro Thr Gln Lys
                180                 185                 190 ccg gta gag gtt ttt gaa cgt atg ctt gag g ct agt agt att cct ggt      624
Pro Val Glu Val Phe Glu Arg Met Leu Glu A la Ser Ser Ile Pro Gly
                195                 200                 205 ttt aca gtt tgt gat cca ttt cta ggt agt g gt tca gcg gct ctt gcg      672
Phe Thr Val Cys Asp Pro Phe Leu Gly Ser G ly Ser Ala Ala Leu Ala
        210                 215                 220 gct att aaa tat gat tgt aac ttt gtt ggt t gc gac att tca gaa caa      720
Ala Ile Lys Tyr Asp Cys Asn Phe Val Gly C ys Asp Ile Ser Glu Gln
225                 230                 235                 240 tct ttt gaa tta tgt agt gaa aga atc caa c aa ttt cta gat aat aac      768
Ser Phe Glu Leu Cys Ser Glu Arg Ile Gln G ln Phe Leu Asp Asn Asn
                245                 250                 255 gtg gat atc ttg gaa aag agt tct aaa aag t aa                          801
Val Asp Ile Leu Glu Lys Ser Ser Lys Lys
                260                 265
```

<210> SEQ ID NO 2
<211> LENGTH: 266
<212> TYPE: PRT
<213> ORGANISM: Micrococcus lylae
<220> FEATURE:
<223> OTHER INFORMATION: At position 138, Xaa = any amino acid

<400> SEQUENCE: 2

```
Met Asn Ser Leu Ser Pro Ser Tyr Thr A la Glu Leu Asn Phe Glu
  1               5                 10                  15

Tyr Lys Ser Asp Asp Asn Ser Pro Arg Arg I le Ser Ile Gln Arg Asn
                 20                  25                  30

Asp Val Ile Ser Phe Leu Lys Ser Leu Pro A sp Asn Ser Val Asp Val
             35                  40                  45

Leu Ile Thr Asp Pro Ala Tyr Ser Gly Met A sn Asn Lys Leu Lys Leu
         50                  55                  60

Gly Lys Gly Arg Ile Val Gly Lys Tyr Ala A sp Lys Gly Thr Glu Gln
 65                  70                  75                  80

Ala Lys Trp Phe Asn Glu Phe Asp Asp Thr G lu Glu Asn Tyr His Gln
                 85                  90                  95

Phe Leu Ser Glu Cys Lys Arg Val Leu Asn L ys Gln Thr Gly His Ile
                100                 105                 110

Tyr Leu Met Phe Asp Ser Phe Ser Leu Leu T hr Leu Gly Ala Leu Val
            115                 120                 125

Arg Glu Tyr Phe Asp Val Lys Asn Leu Xaa V al Trp Asp Lys Val Asn
        130                 135                 140

Ile Gly Met Gly His Tyr Phe Arg Arg Arg H is Glu Leu Ile Leu Phe
145                 150                 155                 160

Ala Thr Asn Gly Asn Thr Arg Lys Val Ser S er Arg Ser Leu His Asp
                165                 170                 175

Ile Trp Asp Val Lys Arg Ile His Asn Ser L ys Tyr Pro Thr Gln Lys
                180                 185                 190

Pro Val Glu Val Phe Glu Arg Met Leu Glu A la Ser Ser Ile Pro Gly
                195                 200                 205

Phe Thr Val Cys Asp Pro Phe Leu Gly Ser G ly Ser Ala Ala Leu Ala
        210                 215                 220
```

| | | | | | | | | | | | | |
|---|---|---|---|---|---|---|---|---|---|---|---|---|
|Ala|Ile|Lys|Tyr|Asp|Cys|Asn|Phe|Val|Gly|Cys|Asp|Ile|Ser|Glu|Gln|
|225| | | | |230| | | | |235| | | | |240|

| | | | | | | | | | | | | |
|---|---|---|---|---|---|---|---|---|---|---|---|---|
|Ser|Phe|Glu|Leu|Cys|Ser|Glu|Arg|Ile|Gln|Gln|Phe|Leu|Asp|Asn|Asn|
| | | | |245| | | | |250| | | | |255| |

| | | | | | | |
|---|---|---|---|---|---|---|
|Val|Asp|Ile|Leu|Glu|Lys|Ser|Ser|Lys|Lys|
| | | |260| | | | |265| |

<210> SEQ ID NO 3
<211> LENGTH: 1671
<212> TYPE: DNA
<213> ORGANISM: Micrococcus lylae
<220> FEATURE:
<221> NAME/KEY: CDS
<222> LOCATION: (1)..(1668)
<223> OTHER INFORMATION: At position 883, N = G, A, C or T
<223> OTHER INFORMATION: At position 904, N = G, A, C or T

<400> SEQUENCE: 3

```
atg gca tcg tta tca aag act aaa cat tta ttt ggt ttt act tca cca      48
Met Ala Ser Leu Ser Lys Thr Lys His Leu Phe Gly Phe Thr Ser Pro
  1               5                  10                  15 cga aca att gaa aaa att att cca gaa tta gat ata ttg agc caa caa      96
Arg Thr Ile Glu Lys Ile Ile Pro Glu Leu Asp Ile Leu Ser Gln Gln
             20                  25                  30 ttt tct gga aag gta tgg ggt gaa aac caa ata aat ttc ttt gat gcg     144
Phe Ser Gly Lys Val Trp Gly Glu Asn Gln Ile Asn Phe Phe Asp Ala
         35                  40                  45 ata ttt aac tcg gat ttc tat gag ggg acc acg tac cct caa gat ccc     192
Ile Phe Asn Ser Asp Phe Tyr Glu Gly Thr Thr Tyr Pro Gln Asp Pro
     50                  55                  60 gct tta gct gcc cgt gat agg ata act aga gct cct aaa gca cta gga     240
Ala Leu Ala Ala Arg Asp Arg Ile Thr Arg Ala Pro Lys Ala Leu Gly
 65                  70                  75                  80 ttt att caa tta aag cca gtt atc caa ttg act aaa gcg ggt aat caa     288
Phe Ile Gln Leu Lys Pro Val Ile Gln Leu Thr Lys Ala Gly Asn Gln
                 85                  90                  95 cta gta aat caa aag agg tta cca gag tta ttt aca aaa caa ttg ctt     336
Leu Val Asn Gln Lys Arg Leu Pro Glu Leu Phe Thr Lys Gln Leu Leu
            100                 105                 110 aaa ttt cag cta cct tca ccc tac cat aca caa tca ccc aca gta aat     384
Lys Phe Gln Leu Pro Ser Pro Tyr His Thr Gln Ser Pro Thr Val Asn
        115                 120                 125 ttt aat gtt cgt cct tac ctt gag tta ctt cga tta atc aat gaa tta     432
Phe Asn Val Arg Pro Tyr Leu Glu Leu Leu Arg Leu Ile Asn Glu Leu
    130                 135                 140 ggt tct ata tct aaa acg gaa ata gct tta ttt ttt ctt caa tta gtt     480
Gly Ser Ile Ser Lys Thr Glu Ile Ala Leu Phe Phe Leu Gln Leu Val
145                 150                 155                 160 aat tac aat aaa ttt gat gag ata aaa aat aag att tta aaa ttt aga     528
Asn Tyr Asn Lys Phe Asp Glu Ile Lys Asn Lys Ile Leu Lys Phe Arg
                165                 170                 175 gaa acg aga aaa aat aat cgc agt gtt agt tgg aag act tat gtt tca     576
Glu Thr Arg Lys Asn Asn Arg Ser Val Ser Trp Lys Thr Tyr Val Ser
            180                 185                 190 caa gaa ttt gaa aag cag att tct att att ttt gca gat gaa gta aca     624
Gln Glu Phe Glu Lys Gln Ile Ser Ile Ile Phe Ala Asp Glu Val Thr
        195                 200                 205 gca aaa aac ttt aga act aga gaa agt tct gat gaa tct ttt aaa aaa     672
Ala Lys Asn Phe Arg Thr Arg Glu Ser Ser Asp Glu Ser Phe Lys Lys
    210                 215                 220 ttt gta aaa act aaa gaa ggg aat atg aag gac tat gca gat gca ttt     720
```

-continued

```
Phe Val Lys Thr Lys Glu Gly Asn Met Lys A sp Tyr Ala Asp Ala Phe
225                 230                 235                 240 ttc cgt tat att cgg ggg aca cag tta gtt a ct att gat aaa aac ctc    768
Phe Arg Tyr Ile Arg Gly Thr Gln Leu Val T hr Ile Asp Lys Asn Leu
                245                 250                 255 cat ctt aaa ata tct agt tta aaa cag gac a gt gtt gat ttt tta tta   816
His Leu Lys Ile Ser Ser Leu Lys Gln Asp S er Val Asp Phe Leu Leu
                260                 265                 270 aaa aat acg gat cgt aat gct tta aat cta a gt tta atg gaa tat gaa   864
Lys Asn Thr Asp Arg Asn Ala Leu Asn Leu S er Leu Met Glu Tyr Glu
                275                 280                 285 aat tat ctt ttt gat cca nat cag tta atc g tt ctt gaa nat aat agt   912
Asn Tyr Leu Phe Asp Pro Xaa Gln Leu Ile V al Leu Glu Xaa Asn Ser
        290                 295                 300 gga ctt att aat agt aaa att aag cag tta g ac gat tct ata aat gta   960
Gly Leu Ile Asn Ser Lys Ile Lys Gln Leu A sp Asp Ser Ile Asn Val
305                 310                 315                 320 gaa tct ttg aaa att gat gat gcg aaa gat t ta tta aat gat ctg gaa  1008
Glu Ser Leu Lys Ile Asp Asp Ala Lys Asp L eu Leu Asn Asp Leu Glu
                325                 330                 335 atc cag cga aaa gct aaa act ata gaa gat a ct gtt aac cat tta aaa  1056
Ile Gln Arg Lys Ala Lys Thr Ile Glu Asp T hr Val Asn His Leu Lys
                340                 345                 350 ctt aga tct gat att gaa gat att tta gac g tc ttt gca aaa att aag  1104
Leu Arg Ser Asp Ile Glu Asp Ile Leu Asp V al Phe Ala Lys Ile Lys
                355                 360                 365 aaa aga gat gtc cca gat gtt cct tta ttc c tt gaa tgg aat ata tgg  1152
Lys Arg Asp Val Pro Asp Val Pro Leu Phe L eu Glu Trp Asn Ile Trp
370                 375                 380 aga gct ttt gct gca cta aat cat aca caa g cg ata gaa ggg aac ttc  1200
Arg Ala Phe Ala Ala Leu Asn His Thr Gln A la Ile Glu Gly Asn Phe
385                 390                 395                 400 att gta gat tta gat gga atg cct tta aat a ca gct cca ggt aag aag  1248
Ile Val Asp Leu Asp Gly Met Pro Leu Asn T hr Ala Pro Gly Lys Lys
                405                 410                 415 cct gat ata gaa att aat tac gga tct ttt t ca tgc att gtt gaa gta  1296
Pro Asp Ile Glu Ile Asn Tyr Gly Ser Phe S er Cys Ile Val Glu Val
                420                 425                 430 act atg tca tca ggg gaa act caa ttt aat a tg gag ggg tct tct gtt  1344
Thr Met Ser Ser Gly Glu Thr Gln Phe Asn M et Glu Gly Ser Ser Val
                435                 440                 445 cca cga cat tat ggt gat tta gtg aga aag g tt gac cat gat gca tat  1392
Pro Arg His Tyr Gly Asp Leu Val Arg Lys V al Asp His Asp Ala Tyr
        450                 455                 460 tgt ata ttt ata gcc cct aaa gtt gcg cca g ga aca aaa gca cat ttc  1440
Cys Ile Phe Ile Ala Pro Lys Val Ala Pro G ly Thr Lys Ala His Phe
465                 470                 475                 480 ttt aac tta aat cga ctt tca aca aaa cat t at ggt gga aaa aca aag  1488
Phe Asn Leu Asn Arg Leu Ser Thr Lys His T yr Gly Gly Lys Thr Lys
                485                 490                 495 att att cct atg tca tta gat gat ttc ata t gt ttc tta caa gtt ggg  1536
Ile Ile Pro Met Ser Leu Asp Asp Phe Ile C ys Phe Leu Gln Val Gly
                500                 505                 510 atc aca cat aat ttt caa gat att aat aaa c ta aaa aat tgg ttg gac  1584
Ile Thr His Asn Phe Gln Asp Ile Asn Lys L eu Lys Asn Trp Leu Asp
        515                 520                 525 aac tta att aat ttc aat tta gaa agc gaa g at gaa gaa att tgg ttt  1632
Asn Leu Ile Asn Phe Asn Leu Glu Ser Glu A sp Glu Glu Ile Trp Phe
        530                 535                 540
```

```
gaa gaa att ata agt aaa att tct aca tgg g ct ata tag                    1671
Glu Glu Ile Ile Ser Lys Ile Ser Thr Trp A la Ile
545                 550                 555

<210> SEQ ID NO 4
<211> LENGTH: 556
<212> TYPE: PRT
<213> ORGANISM: Micrococcus lylae
<220> FEATURE:
<223> OTHER INFORMATION: At position 295, Xaa = any amino acid
<223> OTHER INFORMATION: At position 302, Xaa = any amino acid

<400> SEQUENCE: 4

Met Ala Ser Leu Ser Lys Thr Lys His Leu P he Gly Phe Thr Ser Pro
 1               5                  10                  15

Arg Thr Ile Glu Lys Ile Ile Pro Glu Leu A sp Ile Leu Ser Gln Gln
            20                  25                  30

Phe Ser Gly Lys Val Trp Gly Glu Asn Gln I le Asn Phe Asp Ala
        35                  40                  45

Ile Phe Asn Ser Asp Phe Tyr Glu Gly Thr T hr Tyr Pro Gln Asp Pro
    50                  55                  60

Ala Leu Ala Ala Arg Asp Arg Ile Thr Arg A la Pro Lys Ala Leu Gly
65                  70                  75                  80

Phe Ile Gln Leu Lys Pro Val Ile Gln Leu T hr Lys Ala Gly Asn Gln
                85                  90                  95

Leu Val Asn Gln Lys Arg Leu Pro Glu Leu P he Thr Lys Gln Leu Leu
            100                 105                 110

Lys Phe Gln Leu Pro Ser Pro Tyr His Thr G ln Ser Pro Thr Val Asn
        115                 120                 125

Phe Asn Val Arg Pro Tyr Leu Glu Leu Leu A rg Leu Ile Asn Glu Leu
    130                 135                 140

Gly Ser Ile Ser Lys Thr Glu Ile Ala Leu P he Phe Leu Gln Leu Val
145                 150                 155                 160

Asn Tyr Asn Lys Phe Asp Glu Ile Lys Asn L ys Ile Leu Lys Phe Arg
                165                 170                 175

Glu Thr Arg Lys Asn Asn Arg Ser Val Ser T rp Lys Thr Tyr Val Ser
            180                 185                 190

Gln Glu Phe Glu Lys Gln Ile Ser Ile Ile P he Ala Asp Glu Val Thr
        195                 200                 205

Ala Lys Asn Phe Arg Thr Arg Glu Ser Ser A sp Glu Ser Phe Lys Lys
    210                 215                 220

Phe Val Lys Thr Lys Glu Gly Asn Met Lys A sp Tyr Ala Asp Ala Phe
225                 230                 235                 240

Phe Arg Tyr Ile Arg Gly Thr Gln Leu Val T hr Ile Asp Lys Asn Leu
                245                 250                 255

His Leu Lys Ile Ser Ser Leu Lys Gln Asp S er Val Asp Phe Leu Leu
            260                 265                 270

Lys Asn Thr Asp Arg Asn Ala Leu Asn Leu S er Leu Met Glu Tyr Glu
        275                 280                 285

Asn Tyr Leu Phe Asp Pro Xaa Gln Leu Ile V al Leu Glu Xaa Asn Ser
    290                 295                 300

Gly Leu Ile Asn Ser Lys Ile Lys Gln Leu A sp Asp Ser Ile Asn Val
305                 310                 315                 320

Glu Ser Leu Lys Ile Asp Asp Ala Lys Asp L eu Leu Asn Asp Leu Glu
                325                 330                 335

Ile Gln Arg Lys Ala Lys Thr Ile Glu Asp T hr Val Asn His Leu Lys
```

-continued

```
                    340                 345                 350
Leu Arg Ser Asp Ile Glu Asp Ile Leu Asp Val Phe Ala Lys Ile Lys
                355                 360                 365
Lys Arg Asp Val Pro Asp Val Pro Leu Phe Leu Glu Trp Asn Ile Trp
370                 375                 380
Arg Ala Phe Ala Ala Leu Asn His Thr Gln Ala Ile Glu Gly Asn Phe
385                 390                 395                 400
Ile Val Asp Leu Asp Gly Met Pro Leu Asn Thr Ala Pro Gly Lys Lys
                405                 410                 415
Pro Asp Ile Glu Ile Asn Tyr Gly Ser Phe Ser Cys Ile Val Glu Val
                420                 425                 430
Thr Met Ser Ser Gly Glu Thr Gln Phe Asn Met Glu Gly Ser Ser Val
                435                 440                 445
Pro Arg His Tyr Gly Asp Leu Val Arg Lys Val Asp His Asp Ala Tyr
                450                 455                 460
Cys Ile Phe Ile Ala Pro Lys Val Ala Pro Gly Thr Lys Ala His Phe
465                 470                 475                 480
Phe Asn Leu Asn Arg Leu Ser Thr Lys His Tyr Gly Gly Lys Thr Lys
                485                 490                 495
Ile Ile Pro Met Ser Leu Asp Asp Phe Ile Cys Phe Leu Gln Val Gly
                500                 505                 510
Ile Thr His Asn Phe Gln Asp Ile Asn Lys Leu Lys Asn Trp Leu Asp
                515                 520                 525
Asn Leu Ile Asn Phe Asn Leu Glu Ser Glu Asp Glu Ile Trp Phe
                530                 535                 540
Glu Glu Ile Ile Ser Lys Ile Ser Thr Trp Ala Ile
545                 550                 555

<210> SEQ ID NO 5
<211> LENGTH: 46
<212> TYPE: DNA
<213> ORGANISM: Bacillus stearothermophilus

<400> SEQUENCE: 5
attggatcct aaggaggtga tctaatggac acagaaactg catctg         46

<210> SEQ ID NO 6
<211> LENGTH: 31
<212> TYPE: DNA
<213> ORGANISM: Bacillus stearothermophilus

<400> SEQUENCE: 6
taagtcgact tattcccaaa ataccggttc g                          31

<210> SEQ ID NO 7
<211> LENGTH: 26
<212> TYPE: DNA
<213> ORGANISM: Micrococcus lylae

<400> SEQUENCE: 7
aaattattcc agaattagat atattg                                26

<210> SEQ ID NO 8
<211> LENGTH: 23
<212> TYPE: DNA
<213> ORGANISM: Micrococcus lylae

<400> SEQUENCE: 8
```

```
tcaattgttc gtggtgaagt aaa                                          23

<210> SEQ ID NO 9
<211> LENGTH: 26
<212> TYPE: DNA
<213> ORGANISM: Micrococcus lylae

<400> SEQUENCE: 9
cacagtaaat tttaatgttc gtcctc                                       26

<210> SEQ ID NO 10
<211> LENGTH: 26
<212> TYPE: DNA
<213> ORGANISM: Micrococcus lylae

<400> SEQUENCE: 10
gtgattgtgt atggtagggt gaaggt                                       26

<210> SEQ ID NO 11
<211> LENGTH: 43
<212> TYPE: DNA
<213> ORGANISM: Micrococcus lylae

<400> SEQUENCE: 11
ttaagcttaa ggaggtgatc taatggcatc gttatcaaag act                    43

<210> SEQ ID NO 12
<211> LENGTH: 32
<212> TYPE: DNA
<213> ORGANISM: Micrococcus lylae

<400> SEQUENCE: 12
atttctagac tatatagccc atgtagaaat tt                                32
```